United States Patent [19]

van der Meulen

[11] 4,303,867
[45] Dec. 1, 1981

[54] DOMESTIC APPLIANCE COMPRISING A PROTECTED PROGRAMMING DEVICE

[75] Inventor: Andries van der Meulen, Drachten, Netherlands

[73] Assignee: U.S. Philips Corporation, New York, N.Y.

[21] Appl. No.: 101,973

[22] Filed: Dec. 10, 1979

[30] Foreign Application Priority Data

Dec. 14, 1978 [NL] Netherlands ............... 7812150

[51] Int. Cl.³ .................... H05B 37/02; H05B 41/36
[52] U.S. Cl. ................................. 315/360; 315/119; 328/7; 361/196
[58] Field of Search .............. 315/119, 360, 362; 328/7; 361/195, 196; 307/141, 141.8

[56] References Cited
U.S. PATENT DOCUMENTS 4,189,665  2/1980  van der Meulen ............... 315/360

Primary Examiner—Eugene La Roche
Attorney, Agent, or Firm—Bernard Franzblau

[57] ABSTRACT

A domestic appliance comprises a programming device receiving on-time information and for updating, by way of repetitious signals, the on-time yet to be completed. The repetitious signals continuously activate an activation signal which is independently terminated if the repetitious signals do not appear. When the activation signal is present, first and second switching components are activated so that a discharge tube can emit ultraviolet radiation. A detection element detects whether the first and second switching components are deactivated outside the on-time. If one of the two switching components remains active outside the on-time, the detection element supplies a signal to inhibit the next start signal.

9 Claims, 9 Drawing Figures

DOMESTIC APPLIANCE COMPRISING A PROTECTED PROGRAMMING DEVICE

BACKGROUND OF THE INVENTION

The invention relates to a domestic appliance comprising a power supply connection, a generator tube for generating electromagnetic radiation, first switching means connected in series with the generator tube, and a programming device which comprises an input for receiving on-time information and a subsequent start signal, an output for supplying an activation signal for the first switching means, updating means for updating the on-time yet to be completed, and first detection means for detecting said updating and for generating, in the case of a failure therein, an error signal in order to deactivate said activation signal. A device of this kind is known from U.S. Pat. No. 4,189,665, issued Feb. 19, 1980. This appliance is an irradiation device with a discharge tube for supplying ultraviolet radiation. The discharge tube is filled with a gas or vapour and the radiation generated is used for therapeutic, prophylactic or cosmetic purposes. A plurality of discharge tubes may be present. An excessive does of ultraviolet radiation is particularly undesirable, notably if it is produced because the apparatus is not switched off. In the known device the irradiation time is determined by the discharging of a capacitor via a variable resistor. If the discharge current drops below a given value, the irradiation is terminated. Thus, a single level of protection is provided which becomes ineffective if the switch continuously remains in the closed condition due to a fault. In that case the known device may still be used by providing, for example, an additional external switch in series for example, externally. This pseudo-repair can be performed by the user and results in unprotected operation. Furthermore, the transistor which serves to activate the termination of the radiation could become defective. In that case, operation can be continued with an apparatus which is no longer protected. However, it can still produce correct irradiation times as long as no further fault occurs.

Problems of this kind also occur in, for example, domestic ovens utilizing electromagnetic radiation. The generator is then, for example, a magnetron tube and the wavelength of the radiation used is in the centimeter and decimeter range.

SUMMARY OF THE INVENTION

It is an object of the invention to provide a domestic appliance of the kind described having improved safety features such that the on-time is automatically terminated in the case of discontinuation of said updating, and without the use of complicated solutions which might otherwise be acceptable for expensive installations, such as the provision of double or triple timers. The objects in accordance with the invention are realized in that said updating means comprise a signal output of supplying a periodic signal during said on-time for continually reactivating said activation signal, the activation signal disappearing if said periodic signal does not appear. It has been found that supplying a periodic signal offers a much more reliable way of signalling than the uniform signal used in the known device. If said periodic signal disappears due to a fault, the irradiation also is terminated. The supply of such a periodic signal can be attractively realized by updating the on-time by means of digital devices. Herein, periodic is to be understood to mean that the signal is recurrent. However, the time intervals between occurrence need not always be the same.

Notably in an irradiation device there are preferably provided second switching means for receiving an activation signal together with said first switching means, said generator tube being active only when said first and said second switching means are activated simultaneously. Second detection means are provided for checking said first switching means outside said on-time in order to disable, when said first switching means is in the on condition, a subsequent start signal concerning the activation of said second switching means. Thus, safety is further improved so that reactivation of the second switching means is no longer possible when the first switching means remain in the closed condition. In this respect, for example, the first switching means may conduct the discharge current while the second switching means conduct, for example, the current through a filament electrode. The unprotected starting of a new ontime is thus prevented.

Preferably, said second detection means also act to check said second switching means, outside said on-time, in order to deactivate, when said second switching means are in the on condition, a subsequent start signal concerning the activation of said first switching means. In that case, operation with single protection also cannot occur if the second switching means remain in the closed condition.

FURTHER ASPECTS OF THE INVENTION

Preferably, there are provided third and fourth switching meas, said generator tube being active only when said first, third and fourth switching means are activated simultaneously, there being provided third detection means for checking said third and fourth switching means, outside said on-time, in order to detect any dissimilar condition thereof and to disable in such a case a subsequent start signal concerning the activation of said first switching means. On the one hand, a triple protection can thus be created. On the other hand, said third and fourth switching means may take the form of a protection circuit. In the special case of an oven utilizing electromagnetic radiation, they may be two oven door switches. When the door is opened the activation of the generator tube is immediately terminated. This protection is then double. However, it may occur that one of the door switches becomes defective and indicates per se that the door is closed. This would imply a single and hence inadequate protection. In accordance with the foregoing, such a dissimilar condition is detected (in a situation involving an open door, one of the door switches indicates "closed") and the oven can no longer be used. The correct condition must then be restored, for example, by a service technician.

Preferably, said first and second switching means are connected in series in order to conduct the current through the generator tube in the activated condition. This means that the activation signal can be applied in parallel to the first and second switching means. In that case, only one physical signal has to be realized therefor.

Preferably, there is provided an activation device which comprises an input for receiving said periodic signal and an output of continuously supplying said activation signal under the control of said periodic signal. As a result of such a continuous (DC) activation signal, the switches, for example, remain closed continuously. The conversion of a periodic signal into a DC signal can easily be accomplished using exclusively electronic means.

Preferably, the programming device comprises a microprocessor. This results in a flexible construction because such a microprocessor, having a high processing speed, can also provide a plurality of functions.

Preferably, the programming device comprises an input for receiving an erase the signal for erasing last received on-time information prior to receiving a start signal. In conjunction with the foregoing (separate supply of on-time information and start signal), this is very advantageous because any errors made can thus be readily eliminated prior to the introduction of new on-time information.

Preferably, the programming device comprises an input for receiving an interrupt signal for interrupting said activation signal under the control of said interrupt signal and for supplying a stop signal to the updating device. For example, the irradiation can thus be interrupted while the on-time yet to be completed is memorized. Considering the customary irradiation times (up to, for example, 39 minutes), an interruption mode of this kind may in some cases be desirable.

BRIEF DESCRIPTION OF THE FIGURES

The invention will be described in detail hereinafter with reference to the accompanying drawing in which FIGS. 1a and 1b diagrammatically show circuits for activation of the discharge tube (tubes).

DESCRIPTION OF A PREFERRED EMBODIMENT

Figure 1A:
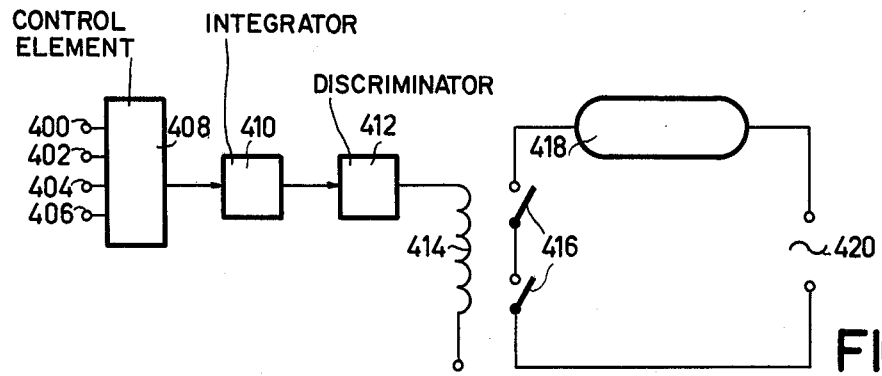
Figure 1B:
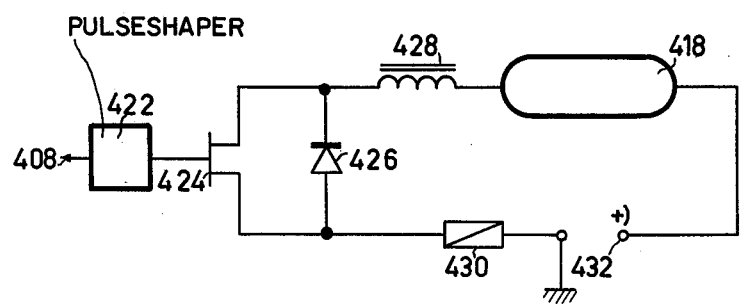

FIG. 1a diagrammatically shows a first circuit for activating the generator tube 418, for example, a discharge tube. Element 408 is a control element which can receive the following signals: at terminal 400 an on-time signal (for example, indicating the number of minutes of irradiation time), at terminal 402 a start signal, on terminal 404 an erase signal, and on terminal 406 an interrupt signal. Normally, first the on-time information is keyed in, possibly followed by an erase signal (if an error has been made), and then new on-time information. Subsequently, the start signal is supplied and shortly thereafter the on-time commences. The operation is interrupted by an interrupt signal, but the on-time yet to be completed is memorized. Restarting is realized by a signal at terminal 402. The terminals 400-406 may form part of the keyboard. During the on-time, the element 408 continuously supplies a periodic signal series. These signals are integrated in element 410, for example, by an RC circuit which has a characteristic time constant which corresponds to several periods of the signal series. Element 412 comprises a discriminator. If the input signal exceeds a given value, the result is a "1"; otherwise, it is a "0". The "1" is amplified sufficiently to energize the coil 414 so that switches 416 are closed. Terminals 420 supply an alternating voltage so that discharge tube 418 is ignited. After expiration of the on-time, the periodic signal series is terminated. This also occurs if the generator for the pulse series becomes defective or if the updating of the on-time yet to be completed stops. It will be found that this can be simply realized in that the element 408 completes a cycle which alternately controls the counting down of the on-time yet to be completed and the supply of a signal to element 410. For the sake of simplicity, it is not shown how it is detected whether one of the two switches 416 remains in the active position in the rest condition of the circuit. FIG. 1b diagrammatically shows a second circuit for activation of the discharge tube. Element 422 receives a pulse series with a suitable ratio of the times at which it is "high" and the times at which it is "low". Element 422 comprises a pulseshaper and activates semiconductor switch 424. When this switch is in the conductive position, the direct current of terminal 432 passes through the series connection of the discharge tube 418, the choke coil 428 and the switch 424. If the switch 424 remains conductive too long, fuse 430 is overloaded, thus forming a circuit interruption. If the series of periodic signals from the element 408 is interrupted, the discharge tube 418 automatically extinguishes. The sequence of operations in the element 408 may be organized in the same manner as in FIG. 1a.

A generator tube for microwaves can be similarly included in an electrical circuit. The activation of such a tube is known per se.

Figure 2:
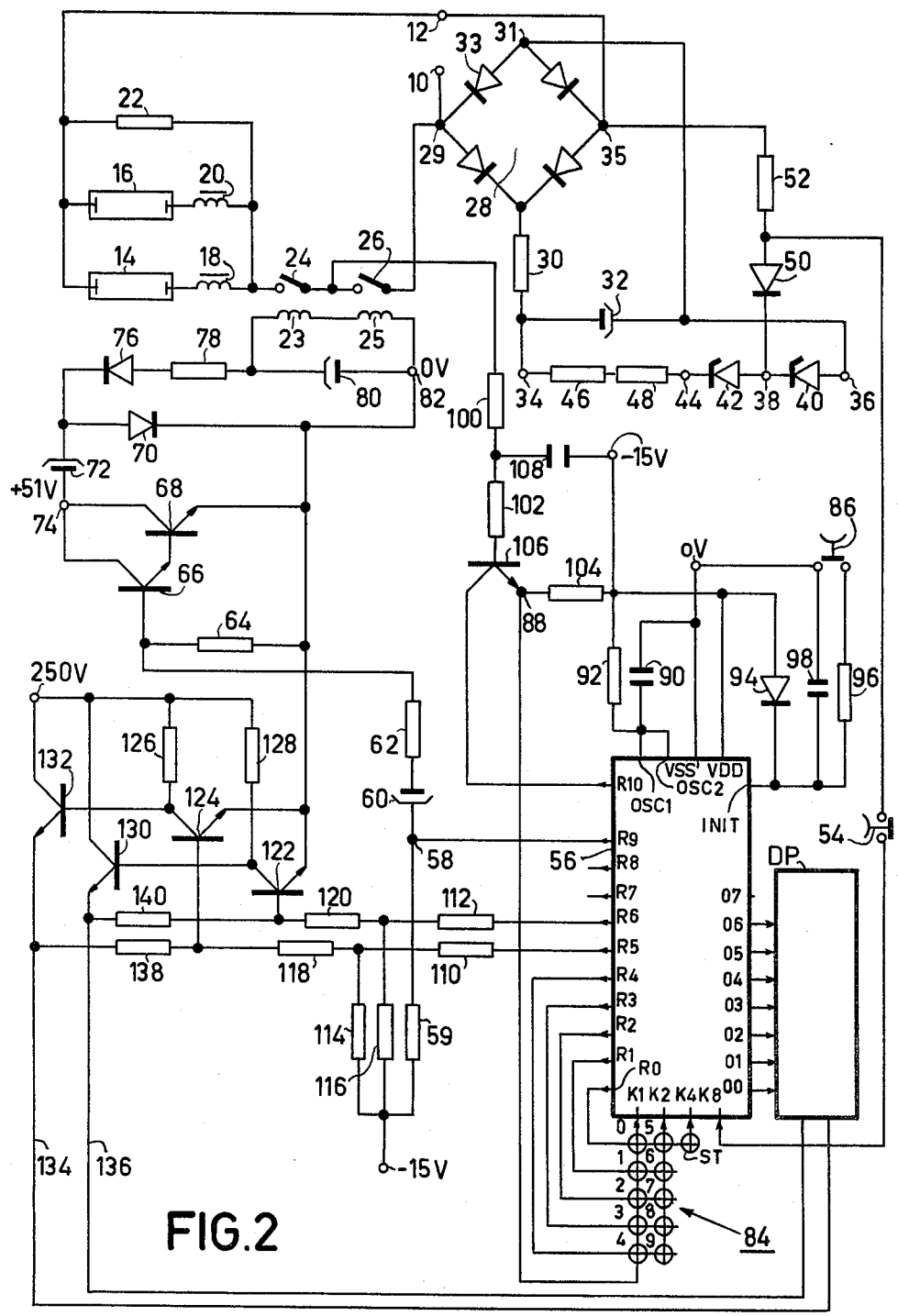
FIG. 2 shows a more detailed diagram of an irradiation device in accordance with the invention.

FIG. 2 shows, by way of example, a further elaborated diagram (partly as a block diagram) in accordance with the general organisation of FIG. 1a. Terminals 10, 12 carry the mains voltage, for example, 220 V, 50 Hz. The circuit is "doubly isolated", but the relevant means therefore are not shown. This means that the control elements in the remainder of the circuit "float" with respect to ground. Furthermore, there are provided two parallel connected a.c. irradiation lamps 14, 16 of a known type, a smoothing coil 18, 20 being connected in series with each lamp. A parallel resistor 22 or 220 kohms is provided to absorb voltage surges. Further components such as starters have been omitted for the sake of simplicity. The two lamps are activated when both series connected switches 24, 26 or the type LCICE, 24 V make OMRON, are in the closed condition. The circuit further comprises a generator for direct voltages. The arrangement 28 is a fullwave rectifier comprising four diodes of the type BY 179. Smoothing is obtained by means of resistor 30 (330 ohms) and capacitor 32 (6.4 microfarads). A voltage difference of approximately 265 volts then exists between the terminals 34 and 36. A Zener diode 40 of the type BZX 79 C 15 produces a voltage difference of 15 volts between the terminals 36 and 38. A Zener diode 42 of the type BZW 87 C 51 produces a voltage difference of 51 volts between the terminals 38 and 44. The resistors 46 and 48 each have a value of 4700 ohms. Via a diode 50 of the type BAW 62 and a resistor 52 of 150 kohms, the terminal 38 is connected to the terminal 12, thus defining a voltage level of approximately 0 volts. Hereinafter, this level is logic "1". The voltage level of terminal 36 is thus approximately −15 volts, which is logic "0" hereinafter. Via connections not shown, the terminals 34, 36, 38, 44 are connected to further components of the circuit. The junction of the diode 50 and the resistor 52 is connected, via an interrupt switch 54, to input K8 of the programming unit 56.

The programming unit 56 is a microprocessor of the type TMS 1000 made by Texas Instruments. For further details, reference is made to the manufacturer's documentation. This microprocessor is particularly suitable for the present purpose because it comprises, inter alia, a programmable logic array (PLA) for activating a digital display device, connections for interrogation and reading of a (simple) keyboard, and a number of control connections for the execution of further functions. First, the activation of switches 24, 26 will be described. Terminal 74 is connected to the voltage of +51 volts (terminal 44). In the rest condition, transistors 66, 68 (BC 546) are blocked, so that substantially the whole voltage of +51 volts is present across capacitor 72 which has a capacitance of 47 microfarads. Terminal 82 carries a potential of 0 volts (terminal 38) and the coils 23, 25 are not energized. Via resistor 64 (2200 ohms), the base electrode of transistor 66 is connected to 0 volts. During the on-time (see hereinafter) the microprocessor 56 continuously supplies pulse-like signals having a width of 1 ms and a frequency of 50 Hz.

These signals appear at output R9 and are applied, via line 58 and coupling capacitor 60 (2.2 microfarads), to the base electrode of transistor 66 (via a resistor 62 which has a value of 5600 ohms). Via resistor 59 of 10 kohms, lead 58 is connected to a potential of −15 volts (element 56 is a p-MOS microprocessor having open collector outputs). Under the control of the above pulse-like signal, the transistors 66 and 68 become conductive and capacitor 72 is discharged. In this situation, diode 76 (type BAW 62) becomes conductive so that, via resistor 78 (39 ohms), the capacitor 80 (capacitance 22 microfarads) is charged, the charge being derived from the capacitor 72. After termination of the pulse on the lead 58, the transistors 66 and 68 are blocked and the capacitor 72 is recharged. The upper electrode (on the side of the diode 76) of the capacitor 72 cannot receive a positive charge as a result of the presence of the diode 70 (type BAW 62). The diode 76 is also blocked after termination of the pulse on the lead 58. The charge on the capacitor 80 is depleted via the coils 23, 25 which have a time constant (RC time) amounting to some tens of milliseconds. Moreover, the switches 24, 26 open only after the voltage across the coils has decreased to a low value (4 volts) instead of the nominal voltage of 24 volts. Thus, a large number of pulses on the line 58 (in the order of 200) may be absent and it is only then that the switches 24, 26 will be opened. This number may be different if a different design is chosen. A pulse may be lacking because the regular completion of the operation cycles in the programming unit 56 is interrupted. As will be described hereinafter, such completion is coupled to the resetting of the on-time yet to be completed, so that the irradiation is then terminated quickly. To those skilled in the art it will be clear that other microprocessors can also be used in an arrangement in accordance with the above. Obviously, the signal on line 58 need not necessarily have a fixed frequency, provided that the series of signals occurs in a regular order and is not interrupted by an excessively long interval.

Hereinafter, the circuit connected to the key-board will be described. The keyboard 84 comprises ten digit keys 0–9 for keying in the on-time information and one key ST for keying in a start signal. The keys 54 and 86 to be described later may also be physically incorporated in the keyboard. It is assumed that at the most one key is depressed at any time. In a given phase of the program of the device 56 (see hereinafter), the output terminals R0-R4 successively carry an interrogation signal. For example, if key 7 is depressed and terminal R2 is activated, it is coupled to input terminal K2. In that case, activation of the terminals R0, R1, R3, R4 does not result in further coupling. The depressed key becomes known to the microprocessor by decoding. Terminal K1 receives a signal from point 88. Terminal K8 may receive a signal from the pause key 54.

The further control and powering of the microprocessor are realized as follows. Terminals OSC1 and OSC2 are interconnected. Terminal VSS is connected to a voltage level of 0 volts (substrate). VDD is connected to a voltage level of −15 volts (supply voltage). Between the terminals OSC1, OSC2 and VSS a capacitor 90 of 47 picofarads is connected and a resistor 92 of 47 kOhms is connected between OSC$\frac{1}{2}$ and terminal VDD. These two components define the clock pulse frequency of the microprocessor to a value of approximately 300 kHz as stated by the manufacturer. Via diode 94 (BAW 62), terminal INIT (for initializing) is connected to a potential of −15 volts, so that it cannot assume a lower potential. Capacitor 98 has a capacitance of 0.47 microfarads and, upon switching on of the apparatus, it must first be charged by a current delivered by terminal INIT. If the potential of the terminal INIT is sufficiently low, the microprocessor is started. When the switch 86 is operated, the capacitor 98 is discharged again via resistor 96 (2200 ohms) and if the potential of terminal INIT subsequently becomes sufficiently low again, a starting action again takes place. In accordance with the internal programming of the microprocessor, the voltage status on the terminal INIT is detected and if this status has the value "0" during six successive periods, a reset signal is produced. In normal circumstances, this terminal is charged to a potential of −15 volts via an impedance present within the microprocessor (which provides an RC time) after switching on of the power.

Hereinafter the circuit will be described for detecting whether one of the switches 24, 26 is in a closed condition outside the on-time of the discharge tubes 14, 16. The means used for this purpose are: the resistors 100, 102, each of which has a value of 330 kohms, resistor 104, having a value of 39 kohms, a transistor 106 of the type BC 546 and a capacitor 108 (0.22 microfarads). Assume that the switch 24 is open and that the switch 26 is closed. The potential of point 29 is then decisive. On the average this potential is higher than that of point 31. At any instant it can never be more than approximately 1 volt lower because diode 33 then would start to conduct. On the other hand, at any given instant it may be higher than the potential of point 31, depending on the phase of the a.c. supply voltage. As a result, capacitor 108 is charged with an RC time of approximately 0.07 s. When terminal R10 of the microprocessor 56 is activated by logic signal "1" (approximately 0 volts), transistor 106 becomes conductive so that the potential of point 88 also becomes logic "1". The latter signal is detected at terminal K1 of the microprocessor 56. If both switches (24, 26) are open in the foregoing case, the signal at point 88, however, is approximately −15 volts, via resistor 104, which always signals a logic "0". In this respect it is to be noted that the tolerances with respect to the value of −15 volts are rather broad so that a difference of a few volts still results in the logic value "0". With respect to the value 0 volts, the deviation may only be a few tenths of a volt. The evaluation of the intermediate range (for example, between $-\frac{1}{2}$ and $-19$ volts) is not guaranteed. On the other hand, if the switch 24 is closed and the switch 26 is open, the potential of point 35 is decisive. Via a similar diode, this point is connected to point 31 so that on average it also has a potential which is higher than that of the terminal 36. The above is again applicable to the state of the transistor 106: the terminal K1 again receives a logic "1". If both switches 24 and 26 are closed, the irradiation tube is activated. If both switches become defective during the on-time so that they cannot be interrupted, the protection has failed. The risk of such a double failure is very small and may be neglected.

The switches 24, 26 may also form part of a protection network, for example, for checking whether the door of a microwave oven is closed. In that case they are operated by the position of the door (instead of by the coils 23/25). For starting the on-time, there is then provided a third switch (not shown) in series with 24/26, and this switch will be controlled by the coils 23/25. If one of the switches 24/26 fails when the door is opened, it remains, for example, in the position "door closed". The switches 24 and 26 thus have a dissimilar condition. This can be detected by activation of terminal R10, the error signal on terminal K1 introducing an "error" bit in the memory of the microprocessor. This error bit cannot be corrected by the normal program of the microprocessor, but must be set to the condition "correct" by a service technician, by way of a service program, after replacement of the faulty door switch. The terminal R10 can be activated, for example, once every 10 seconds. If the dissimilar condition is detected two or three time in succession, the "error" bit is definitely introduced (the first detection is then provisional).

The display circuit will now be described. For this purpose, the microprocessor comprises two selection outputs R5, R6. Also provided are seven code signal outputs 00-06 which are controlled, by way of the internal programmable logic array (PLA), for activation of a seven segment display device. For the sake of brevity, this device is represented as a block DP and will be described in detail hereinafter. The selection outputs R5, R6 are connected, via resistors 110, 112(47 kohms), and 114, 116, 118, 120 (all 33.2 kohms), to a potential of $-15$ volts or the base electrode of transistors 122, 124 (type BF 422). The emitter electrodes thereof are connected to point 82 (potential 0 volts). The collector electrodes thereof are connected, via resistors 126, 128 (value 330 kohms), to a power supply potential of 250 volts (terminal 34). The latter is suitable for activation of the actual display elements. If the terminals R5, R6 carry a low potential, the transistors 122, 124 are driven by the $-15$ volts supply voltage so that the collector electrodes thereof carry a low potential. As a result, the transistors 130, 132 are cut off and the lines 134, 136 are maintained at a low potential via resistors 138, 140 (value 681 kohms). The display elements are then in the non-selected condition. If the transistors 122, 124 are driven further by a high signal on the terminals R5, R6 (approximately 0 volts), the high potential of their collector electrodes ensures that the corresponding transistor 130 or 132 (type BF 422) also becomes conductive, and that the relevant lead 134 or 136 is controlled to a high potential. Via this lead, the display power is supplied to the display element. Hereinafter, first the actual display device will be described and subsequently the machine program. It is to be noted that the connections R7, R8, 07 of the microprocessor 56 are not connected to further parts of the circuit. They are available for realizing further functions, if required.

Figure 3:
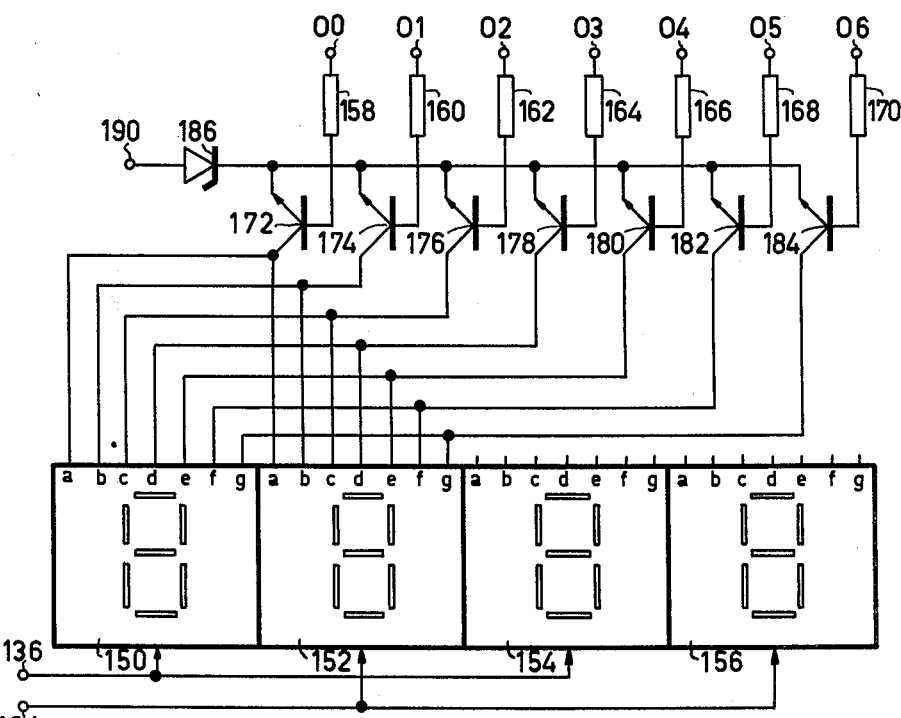
FIG. 3 shows a detail of the display device in accordance with FIG. 1.

FIG. 3 is a detailed representation of the display device DP of FIG. 2. The circuit comprises the connections 00-06 and 134, 136 of FIG. 2 and a power supply connection 190 which receives $-15$ volts. The actual display is realized by means of four display elements 150, 152, 154, 156. These elements are seven-segment gas (plasma) elements of the type Philips ZM1550. The selection connections are denoted by the letters a-g. The elements 150 and 154 are driven completely in parallel, also as regards the connections a-g. The same is applicable to the elements 152, 156. The resistors 158-170 have a value of 330 kohms, the transistors 172-184 are of the type BC 546, and the zener diode 186 is of the type BZX 79 C 6 V2. Thus, the same information is displayed twice; once in the direction of the operator (who may be standing in front of the apparatus) and once in the direction of the person being irradiated (this may be the opposite direction). The display elements are periodically activated, but the appearance of a continuous display is obtained by an after-glow effect.

A current limiting resistor of 7620 ohms should be included in each supply lead for the display leads.

Figure 4:
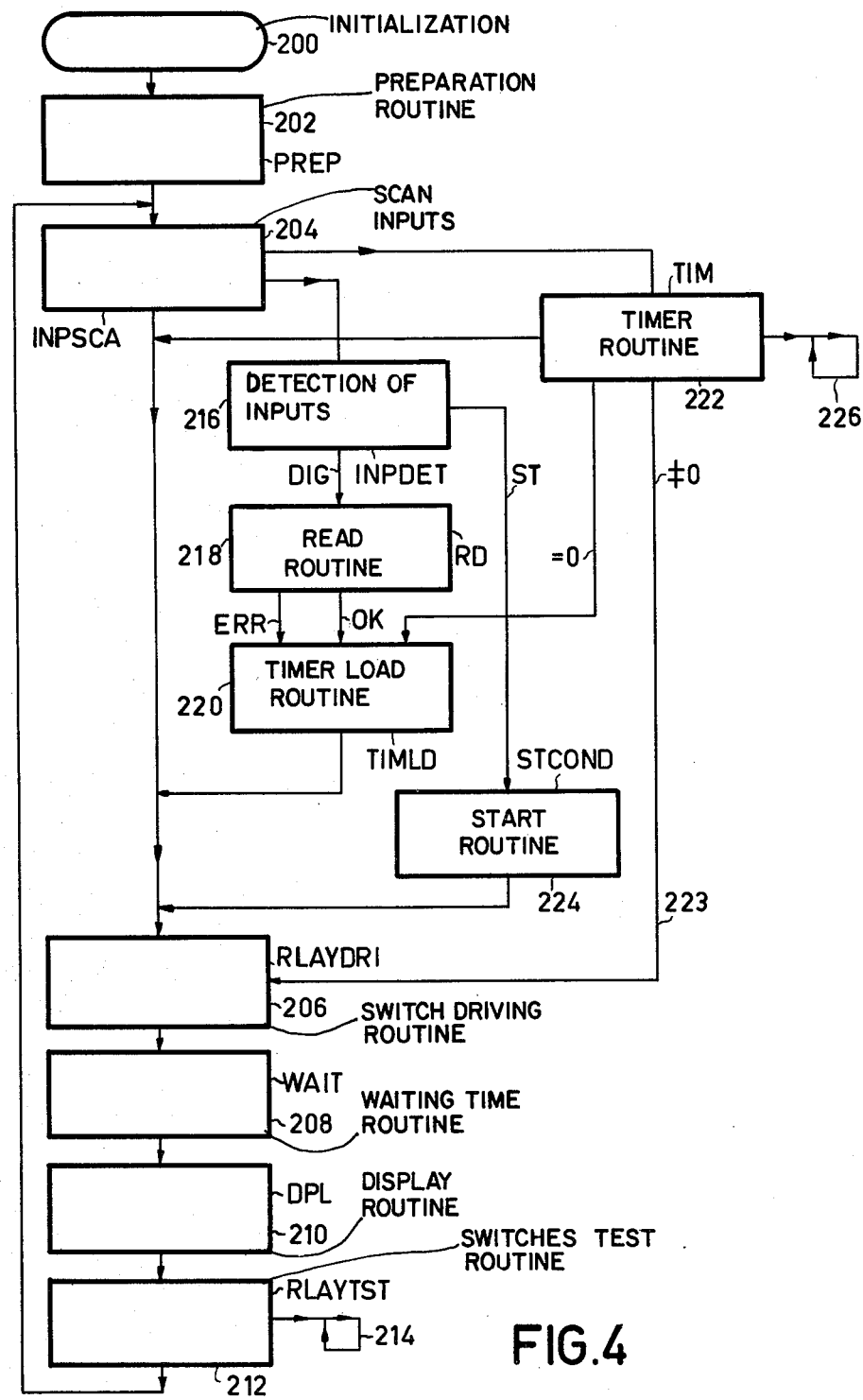
FIG. 4 diagrammatically shows the flow diagram on which the operation of the device shown in FIG. 2 is based.
Figure 6:
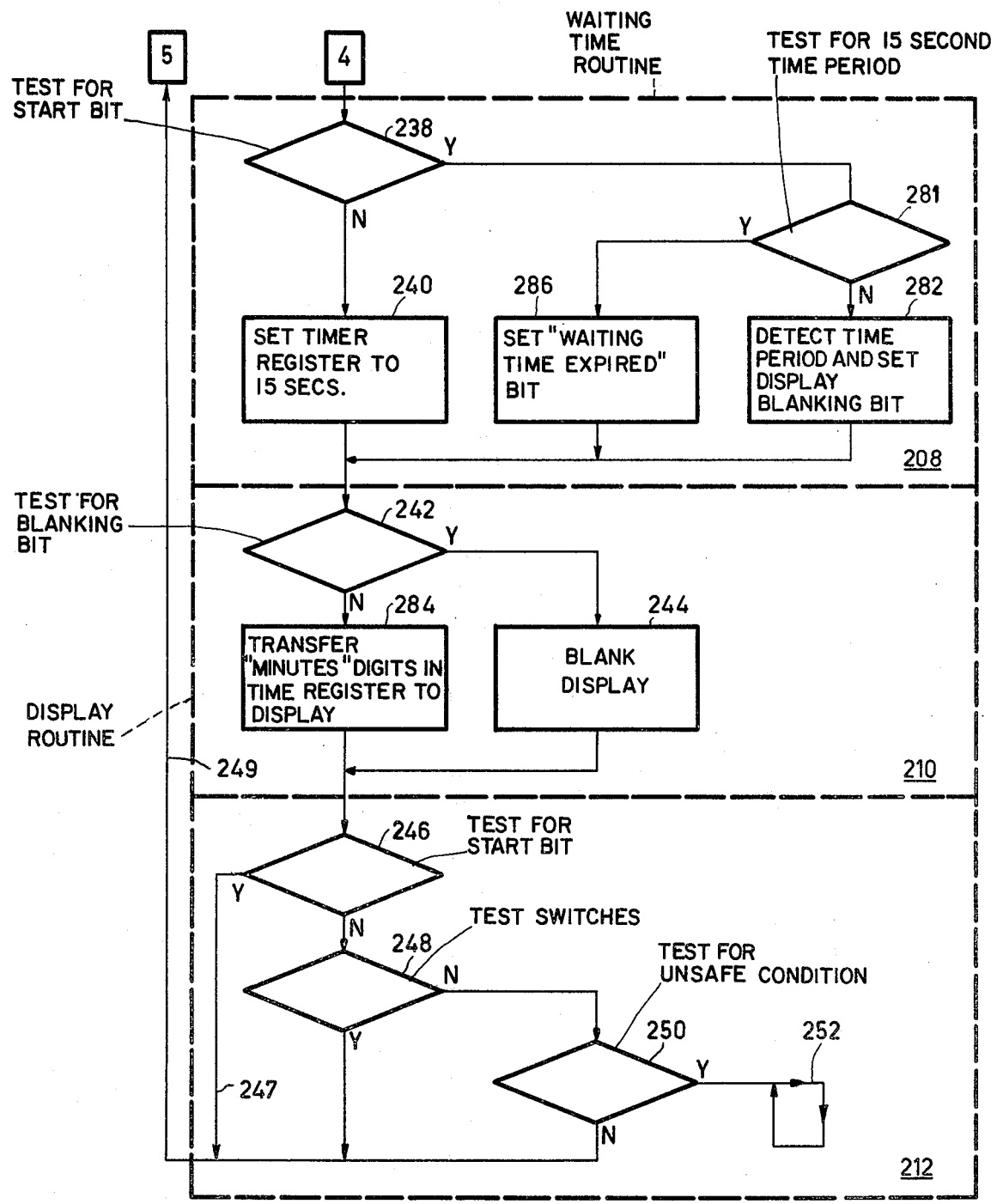
FIG. 6 shows a second part of a detail of FIG. 4.
Figure 7:
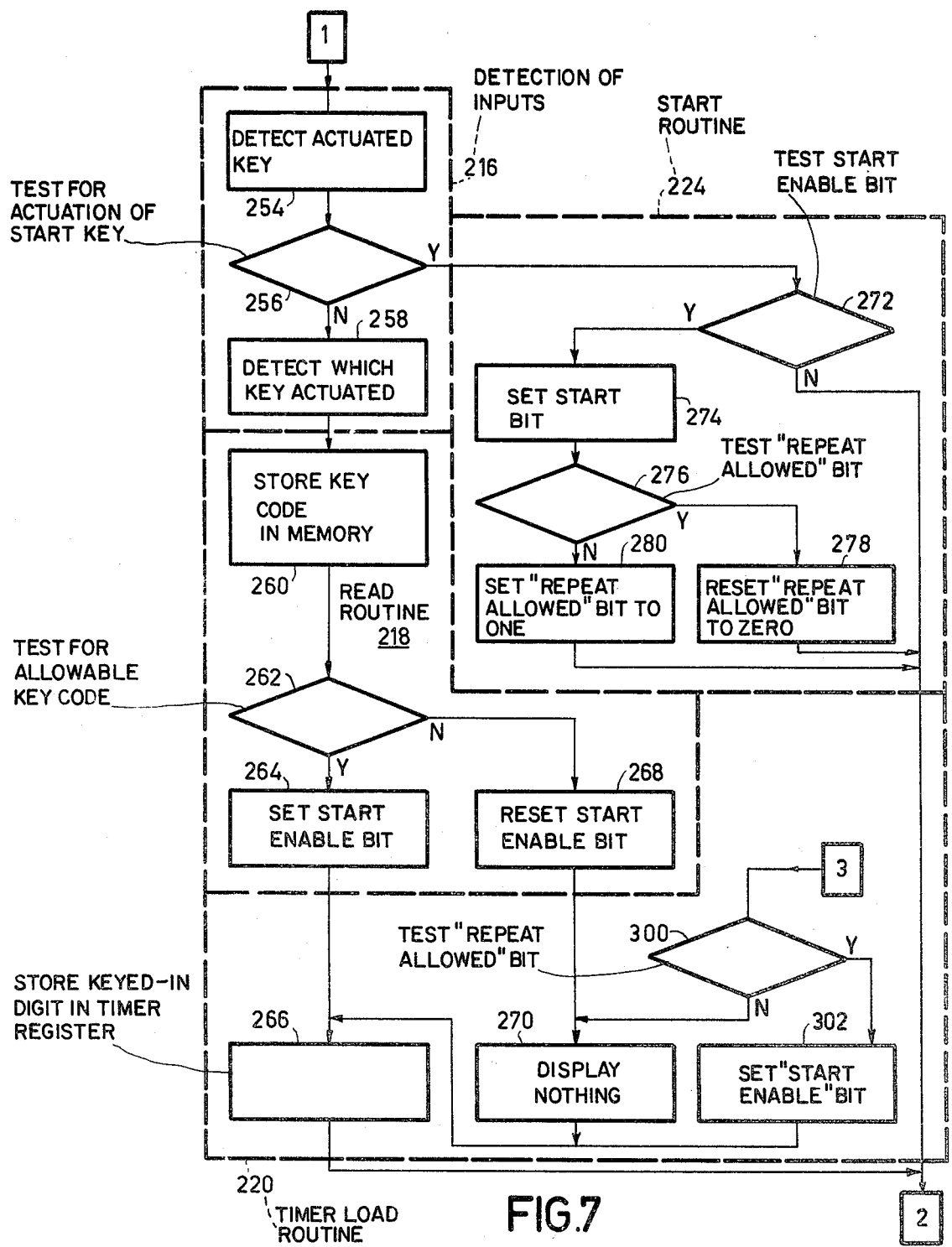
FIG. 7 shows a third part of a detail of FIG. 4.

FIG. 4 diagrammatically shows an overall flow diagram of the subroutines underlying the operation of the device in accordance with FIG. 2. The diagram will be elaborated at a later stage with reference to the FIGS. 5-8. The organization diagram comprises an input which is denoted by the reference 200 and which is subject to the condition that a supply voltage is present. From this point, the path extends to block 202; the enable routine. Therefrom, a path extends to block 204, the routine for sampling of the input signals. Therefrom, paths extend to block 206: relay energizing routine: to block 216, routine of detecting the input data and to block 222, the routine for the time indicator (or updating device). From block 206, a path extends to block 208, waiting time routine. From block 208, a path extends to block 210, display routine. From block 210 a path extends to block 212, the routine for the testing of the switches (24, 26 in FIG. 2). From block 212, a first path extends to block 214, relay unsafe, and a second path back to block 204 (see above). From block 216, a path extends to block 218, write routine, and to block 224: routine of the start condition. From block 218, a path extends to block 220, loading routine for the time indicator. From block 220, a path extends to block 206. From block 222 first path extends to block 220, a second path to block 206 (223) and a third path to block 226, updating device defective. From block 224, a path extends to block 206. The procedure will be described in detail with reference to the FIGS. 5, 6, 7.

Figure 8:
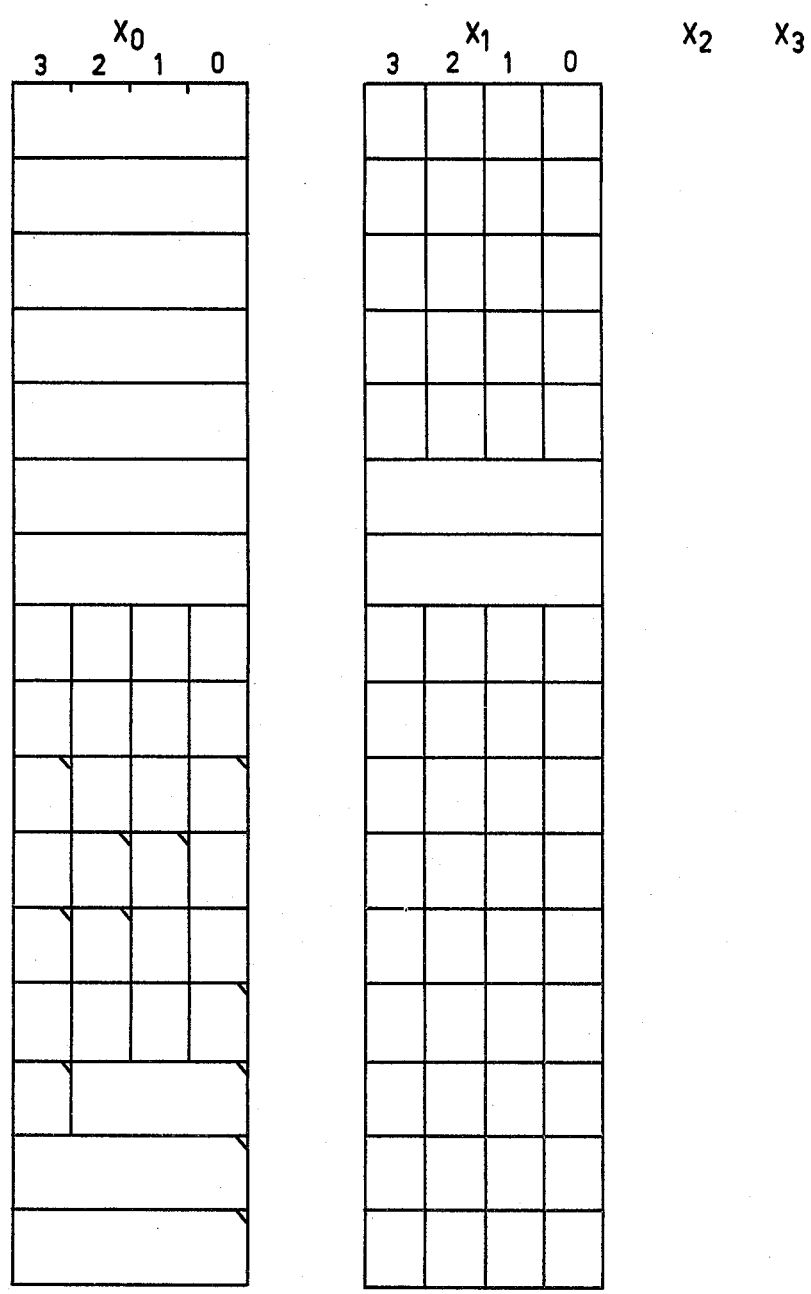
FIG. 8 illustrates the content of the microprocessor memory for FIG. 2.

FIG. 8 illustrates the content of the read/write memory section of the microprocessor 56 of FIG. 2. The capacity is 4 banks of 16 U-bit words each. The bank addresses are supplied by the so-called X register. Only the first two banks will be considered. The words are addressed by the so-called Y register. The words Y6-Y11 of the bank 0 contain the time yet be completed, i.e. successively: the number of tens of minutes, the further number of minutes, the number of tens of seconds, the further number of seconds, the further number of 1/5 seconds, and finally the further number of 1/50 seconds.

The word Y9 is the start work and contains successively the start bit (for the time indicator), 0, 0 and the enable bit for the starting. Word Y10 contains successively 0, the "first time" bit, the "50 Hz block" bit, and 0. Word Y11 contains 0, 0, the "waiting time expired" bit, and the display blanking bit. Word Y12 contains the sample bit for the output information, 0, 0, 0. Word Y13 contains three bits which act as a counter against jittering of key contacts, and the input blocking bit. Words Y14 and Y15 contain eight bits which together form a counter position for the safety test. Word Y0 contains the data of the last R output signal during the sampling of the input data. In bank X1, words Y5, Y6 contain time setting data in minutes and tens of minutes, respectively, in the same way as the words Y5, Y6 and bank X0. The other parts of the memory are not used in this embodiment.

Figure 5:
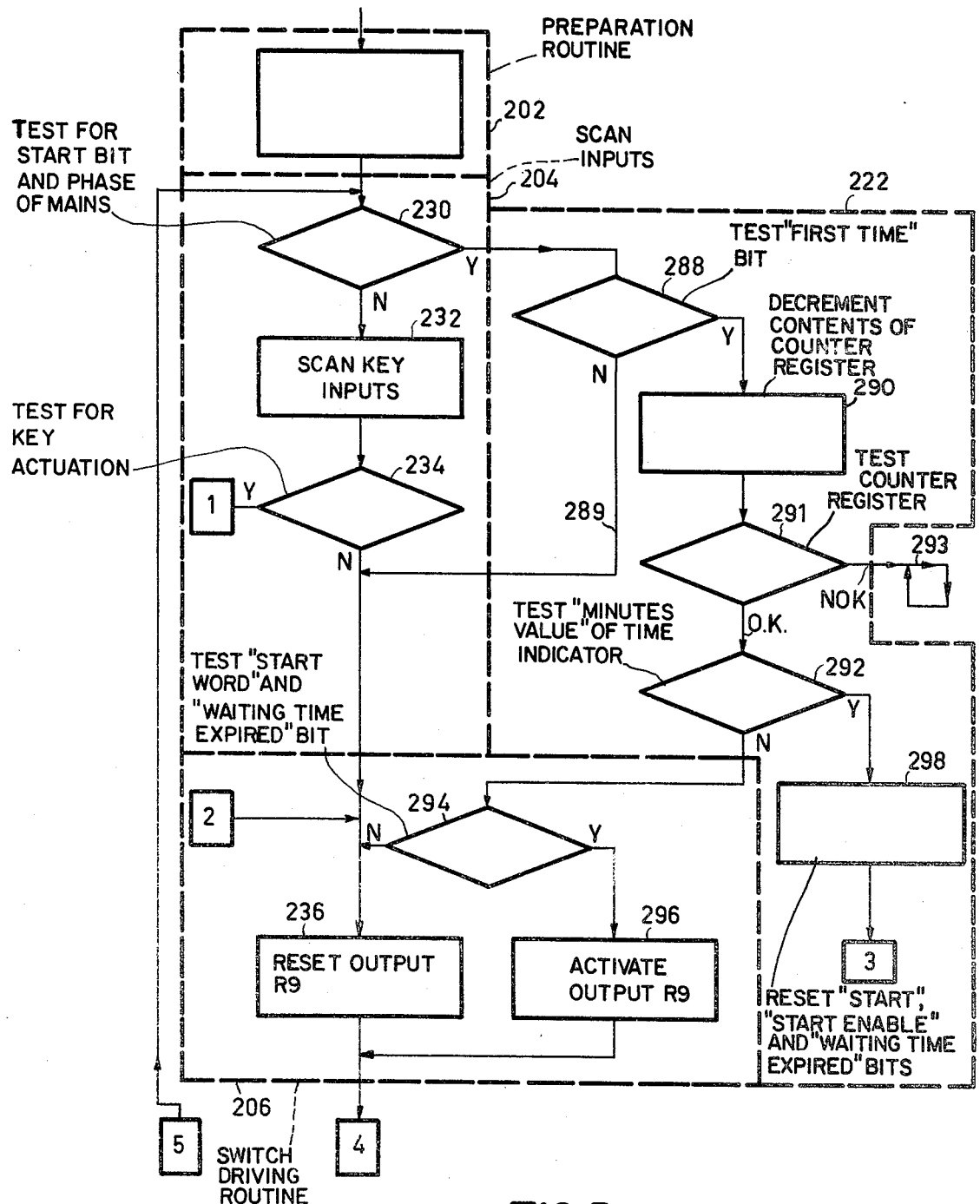
FIG. 5 shows a first part of a detail of FIG. 4.

FIG. 5 shows a first part of a detail of the diagram of FIG. 4. As has already been stated, routine 202 is started if the supply voltage, notably the voltage of −15 volts, is present at terminal 36 and the voltage of 0 volts is present at terminal 38 in FIG. 2. The internal clock in the microprocessor 56 is thus started. The enable routine is started in response to said signal on terminal INIT and performs the following non-conditional operations:
1. the registers of the microprocessor are reset. 2. the time indication (situated in the minutes section of the updating device, see hereinafter) is then "00", but on the display device this information is displayed as two strokes on the centre horizontal segments: thus, "nothing" is displayed. This is realized in that the blanking bit for the display device (word Y11) is made equal to "1" so that the actual 4-bit code for the display elements is then "1111". Via the output device (PLA) of the microprocessor 56, this is translated into the 8-bit code 0100-0000. Block 202 has a single output connected to block 204, the routine for the sampling of the input signals. In block 230 it is tested whether the start bit (word Y9) of the time has been set and whether the positive phase of the 50 Hz mains voltage is present. Initially, these conditions, (to be combined by an AND function) will not both be satisfied (notably the start bit=0). In block 232, the key inputs of key board 84 of FIG. 2 are sampled by interrogation of the outputs R0-R4 of the microprocessor. The input K8 connected to switch 54 is then automatically taken into account. The data received is stored in the accumulator register of the microprocessor 56. In block 234 it is detected whether a key is depressed, i.e. whether the content of the accumulator register does not equal zero. Initially, no key will be depressed (result of the test: negative). In that case a change-over is made to block 206, the relay energizing routine. In block 236, the output R9 of microprocessor 56 is made logic "0". Initially, this will be a dummy operation because this information already had the value "0". Therefore, a change over is made to block 208, the waiting time routine. The waiting time is the time which expires between the operation of the start key and the actual switching on of the irradiation source. In block 238 (FIG. 6) it is tested whether the start bit has been set (see also block 230). Initially, this will not be the case. In block 240, the seconds section (word Y3) of the register of the time indicator is filled with data: 15 seconds. This is the value (11) of the waiting time. Moreover, a further section (word Y4) of the register of the time indicator is filled with the data: 60 seconds (0110). Thus, the irradiation time adjusted in the register becomes 1 minute too long. This offers the advantage that the position 0 minutes, 60 seconds can be used for detection of the end of the irradiation time. Subsequently, the change over to block 210 is made, the display routine. In block 242, it is first tested whether the blanking bit for the display device has been set to 1. This bit controls the flashing of the display during the waiting time. Thus, initially this bit (in the word Y11) will not have been set to 1. In block 284, the data of the minutes register of the time indicator is applied to the display device in two operations, via a multiplex organization. Initially, this will result (see block 202 above) in display on the central two horizontal elements of the display device. Multiplexing is controlled by the first bit of the word Y12. If the blanking bit has the value "1" (this is so every other second during waiting), the display in block 244 is blanked. The afterglow time of the display elements is much shorter than 1 second, so that the display "flashes". Subsequently, the change over to block 212 is made, the routine for the testing of the switches. it is first tested in block 246 whether the start bit has been set (see block 238). If the start bit has not been set to "1" (which will originally be the case), it is tested in block 248 whether the switches are "safe" (via output R10 and intput K1), that is to say whether they are both in the open condition (the chance that both switches are closed is neglected). Normally, the switches will be safe and a changeover will be made to line 249. If they are not safe, a counting sum in the words Y14, Y15 is incremented. Subsequently, it is tested in block 250 whether the unsafe condition has prevailed for some time already, for example, in that said two words generate an overflow signal in reaction to incrementation. This time can be reached, for example, after 1.3 seconds. Initially, this time will not have expired and a changeover is also made to line 249. If the time has expired, a change over is made to loop 252 which can be completed an unlimited number of times, for example, under the control of a command: return to the same instruction. The loop can be left only if the mains voltage is switched off and will generally be reached again when another changeover takes place. The described loop (blocks 204-206-208-210-212) can be completed an arbitrary number of times and constitutes an initial waiting loop. Completion of this waiting loop always requires a given period of time. As a result of this period of time, the words Y14, Y15 require only a limited capacity for counting down 1½ seconds. The first chance can be realized by depression of a key on the keyboard 84 in FIG. 2. In that case, a change-over to block 216 in FIG. 7 takes place in block 234, the routine for detecting the input information. In block 254, it is first of all detected which key has been actuated. If a new key is actuated, the fourth bit of Y13 is made equal to "0". If the same key is detected again during the completion of the loop, the sum of the first three bits of the word Y13 is incremented by one unit. If an overflow condition arises, a "real" key is concerned which may be processed. If no key or another key is detected during the completion of the loop, the word Y13 is reset to zero. Thus, no adverse effects are experienced from bouncing of the keys. When the key has been processed, the fourth bit of the word is set to "1" in order to block a second processing operation. In block 256 it is tested whether the start key (ST in FIG. 2) has been actuated. This will not be the case when the operation is correct and so the depressed digit key will be detected in block 258. This digit is decoded and subsequently a change over is made to block 218, the write routine. The keyed-in digit is then stored in digital code in block 260 in the memory location of the time setting, bank X1, work Y5 of the memory. The first key is the most significant key, and the key "0" is ignored. In block 262, it is first tested whether the key is permissible. The first key is always permissible, provided it is not the "zero" key. This "0" would then be translated into "1111" (i.e. 15) and again result in the display: "nothing". Furthermore, in block 260 the repeat bit (in word Y10, second bit) is set to the position "repeat possible", i.e. "0". When a key having a permissible digit value has been operated, the enable bit for starting is subsequently made equal to "1" in block 264. Subsequently, a change over takes place to block 220, loading routine for the time indicator. In block 266 exclusively the keyed-in digit is stored in the register (minutes section) of the time indicator, bank X0, word Y5 of the memory. Subsequently, a change over occurs to block 206 in FIG. 5. The described excursion to FIG. 7 takes place only once for each keying operation. The main loop consisting of blocks 204-206-208-210-212 may be repetitively cycled until the key is released and a further key (possibly the same key) is actuated. The key first depressed is then displayed in the least-significant position. When a second digit key is depressed, the same thing takes place as when the first key is depressed: the second digit becomes the least significant digit, while the first digit depressed is transferred to the most significant position (word location Y6) and is displaced accordingly. In block 262 a check for correct operation is performed. The operation is correct if at the most two digit keys have been depressed successively (one key, however, is sufficient already), and if the value of the irradiation time is correct (at the most 39 minutes). If an excessive irradiation time is detected when the second key is depressed (more than 39 minutes) of if a third key is depressed, which would produce an irradiation time of between 40 and 399 minutes, the enable bit for starting is reset to zero in block 268 and the information "nothing" is again displayed by way of two horizontal strokes (the latter in block 270). From block 270 there is again the change over to block 266 and subsequently to block 206 in FIG. 5.

In second or third instance the start key may be depressed. In that case, in FIG. 7 a change over takes place from block 216 to block 224, the routine of the starting condition. First it is tested in block 272 whether the enable bit for starting has the value "1". This bit has been set to "1" in block 264. However, if it has not been set to "1", a change over is made back to block 206 in FIG. 5. If this had been set to "1", the start bit is set to "1" in block 274. In block 276 it is tested whether the bit "repeat possible" (second bit of word location Y10) has the value "0" or "1". This bit has been set to zero in block 260. If the first time is concerned, this bit is now set to "1" in order to indicate that repetition is possible (block 278). If it was "1", however, it is reset in block 280: repetition is no longer possible. The outputs of blocks 278 and 280 are connected to block 206 in FIG. 4. Via this bit "repeat possible", two equally long irradiations can be successively activated without the time programming having to be adjusted again for the second time. In the case of switching on and when the adjusted time is changed, this bit is always set to zero (in block 260). Said repetition can thus be omitted.

The start bit has thus been set. As has already been stated, it can be tested in the blocks 230, 238 and 246 in FIGS. 5, 6. First, a branch connection can be made from block 238 to block 281. Therein, it is tested whether the time of 15 seconds generated in block 240 has already expired (this time is counted down in block 222). If the start bit has not yet been set to "1", this time is set again for each passage through the block 240. If said 15 seconds have not yet expired, a change-over is made from block 281 to block 282. Therein, it is detected whether the time value in seconds (in word Y3) is even or odd. If the time is even, the display blanking bit is set to "1". If the time is odd, it is set to "0". Subsequently, a change over is made again to block 210, the display routine. The display blanking bit in block 210 is then either "0" or "1", so that either block 244 is completed (in which case the display is blanked), or the block 284 is completed. In block 284, the digits in the minutes section of the register of the time indicator are applied to the display device. The display thus flashes for 15 seconds. After expiration of the 15 seconds (test in block 281), the bit "waiting time expired" is set in block 286. For the remainder, the loop closed by the line 249 is repeatedly completed. The relay is no longer tested in block 212, because the output to line 249 results directly from block 246 (output 247). As a result of the multiplexing in block 284, two loops must be completed each time for the display of the complete number.

Said counting down takes place in block 222. Furthermore, in block 230 the start bit for the time indicator is then "1" and the chance that the 50 Hz mains voltage is also in the positive phase is 50%. If it is in the positive phase, a change over takes place from block 230 to block 288. Therein, it is detected whether a "first time bit" (third bit of word Y10) has the value "0". If it has the value "0", a change over takes place to block 290. In block 290, the content of the counter register (word locations Y0-Y6) is counted down by 1/50 seconds. Moreover, in block 290 said "first time bit" is reset to 1. The setting (to "0") of this first time bit takes place in block 232. In block 291 it is detected whether the counter registers function properly. This is realized as follows:

first the counter position is fetched from the memory, after which it is applied to the accumulator of the microprocessor where it is reduced by 1 (i.e. by 1/50 second). Subsequently, this position is stored again in the memory. Finally, it is checked whether the sum in the accumulator equals the sum newly stored in the memory. If this is not the case, a change over is made to loop 293 which operates as an end loop. Thus, the updating is checked. If the test is "true", it is tested in block 292 whether the munites value of the time indicator is "0". If this is not the case, output to block 294 takes place. In block 294 the following conditions are tested:

(a) does the start word (word Y9) have the correct value (i.e. "1001")

(b) does the bit "waiting time expired" have the value "1" (set in block 286). If the test is "false", a change over to block 236 takes place: output R9 (and hence the switches 24, 26) is no longer activated by said 1 kHz pulse series. If they were activated until then, the activation is terminated. If the test in block 294 is "true", a change over takes place to block 296. The output R9 is activated and the irradiation commences. When the indicator in block 292 indicates the value "0 minutes", the irradiation time has been completed (this is because 60 seconds had been added previously. A change over to block 298 then takes place; therein, the start bit for the time indicator, the enable bit for the starting and the bit "waiting time expired" are set to "0" and the irradiation has been completed. The output R9 is no longer activated after the next passage through block 206. Subsequently, a change over takes place to block 220 in FIG. 7, loading routine for the time indicator. First it is tested in block 300 whether the bit "repeat possible" has the value "true". If this is the case, the enable bit of the start is set again in block 302. Subsequently, a change over to block 266 takes place. If said enable bit has the value "false", the time setting is set to zero in block 270 with the display blanking as for the output of block 202. In block 266, the minutes section of the register (words Y5, Y6 in bank X1) is set to zero. The initial condition has thus been restored.

The word Y0 of bank X0 serves as a counter register for indicating which one of the R outputs has been activated last for the sampling of the keyboard. The reset key 86 has already been discussed. This key operates for "on/off" switching of the microprocessor so that all registers are erased. The interrupt key operates as follows: it sets the start bit to "0" (first bit of word Y9). As a result, the start word is no longer correct so that the block 222 is no longer reached, and neither is the block 296. As a result, the energizing of the relay is terminated (block 236). The irradiation is then terminated while the irradiation time yet to be completed is memorized (unless an incorrect key is subsequently depressed). Restarting can be realized in the normal manner by means of the start key. If the reset key is depressed during irradiation, the remaining irradiation time cannot be memorized.

What is claimed is:

1. A domestic appliance comprising, a power supply terminal, a generator tube for generating electromagnetic radiation, first switching means connected in series with the generator tube to said supply terminal, and a programming device which comprises an input for receiving on-time information and a subsequent start signal, an output for supplying an activation signal for the first switching means, updating means for updating the on-time yet to be completed, and first detection means for detecting said updating and for generating, in the case of a failure therein, an error signal in order to deactivate said activation signal, and wherein said updating means comprise a signal output for supplying a periodic signal during said on-time for continuous reactivation of said activation signal, the activation signal disappearing if said periodic signal does not appear.

2. A domestic appliance as claimed in claim 1 which comprises an irradiation device, said irradiation device further comprising second switching means for receiving said activation signal together with said first switching means and connected in circuit so that said generator tube can be active only when said first and second switching means are activated simultaneously, second detection means for checking said first switching means outside said on-time in order to de-activate, when said first switching means are in the switched on condition, a subsequent start signal for the activation of said second switching means.

3. An irradiaton device as claimed in claim 2, characterized in that said second detection means also checks said second switching means outside said on-time in order to deactivate, when said second switching means are in the switched on condition, a subsequent start signal for the activation of said first switching means.

4. A domestic appliance as claimed in claim 1 further comprising third and fourth switching means connected in circuit so that said generator tube is active only when said first, third and fourth switching means are activated simultaneously, and third detection means for checking said third and fourth switching means outside said on-time in order to detect any dissimilar condition thereof and to disable in such a case a subsequent start signal for the activation of said first switching means.

5. An irradiation device as claimed in claim 3, characterized in that said first and second switching means are connected in series in order to conduct a current through the generator tube in the activated condition.

6. An irradiation device as claimed in any one of the claims 1 to 5, further comprising an activation device which comprises an input for receiving said periodic signal and an output for continuously supplying said activation signal under the control of said periodic signal.

7. An irradiation device as claimed in any one of the claims 1 to 5 wherein the programming device comprises a microprocessor.

8. An irradiation device as claimed in any one of the claims 1 to 5 wherein the programming device comprises an input for receiving an erase signal for erasing the last received on-time information prior to receiving a start signal.

9. An irradiation device as claimed in any one of the claims 1 to 5 wherein the programming device comprises an input for receiving a pause signal for interrupting said activation signal under the control of said pause signal, and for supplying a stop signal to the updating device.

* * * * *